(12) United States Patent
Yamine et al.

(10) Patent No.: US 12,151,054 B2
(45) Date of Patent: Nov. 26, 2024

(54) METHODS OF AUTOMATED GARBAGE CHUTE AIR EVACUATION TO IMPROVE AIR QUALITY

(71) Applicants: Elias Yamine, Tulsa, OK (US); Alexander Yamine, Tulsa, OK (US)

(72) Inventors: Elias Yamine, Tulsa, OK (US); Alexander Yamine, Tulsa, OK (US)

( * ) Notice: Subject to any disclaimer, the term of this patent is extended or adjusted under 35 U.S.C. 154(b) by 387 days.

(21) Appl. No.: 17/762,168

(22) PCT Filed: Sep. 18, 2020

(86) PCT No.: PCT/US2020/051470
§ 371 (c)(1),
(2) Date: Mar. 21, 2022

(87) PCT Pub. No.: WO2021/055733
PCT Pub. Date: Mar. 25, 2021

(65) Prior Publication Data
US 2022/0370676 A1    Nov. 24, 2022

Related U.S. Application Data

(60) Provisional application No. 62/902,569, filed on Sep. 19, 2019.

(51) Int. Cl.
*B01D 53/22*    (2006.01)
*A61L 9/20*    (2006.01)

(52) U.S. Cl.
CPC ............ *A61L 9/20* (2013.01); *A61L 2202/11* (2013.01); *A61L 2202/14* (2013.01); *A61L 2209/14* (2013.01)

(58) Field of Classification Search
CPC .... A61L 2202/11; A61L 9/20; A61L 2202/14; A61L 2209/14
See application file for complete search history.

(56) References Cited

U.S. PATENT DOCUMENTS 5,277,136 A * 1/1994 Davis .................. A61L 2/04
110/110
5,407,470 A    4/1995 Jutzi
(Continued)

OTHER PUBLICATIONS

International Search Report of PCT/US2020/051470 dated Feb. 5, 2020 [PCT/ISA/210].
(Continued)

*Primary Examiner* — Anthony R Shumate
(74) *Attorney, Agent, or Firm* — Sughrue Mion, PLLC

(57) ABSTRACT

This description relates to waste disposal garbage chutes and more particularly to automated air quality management in and around the disposal chute and collection rooms where garbage chutes are present utilizing automated air quality sensing hardware and evacuation devices to provide a clean, sanitary waste room environment. A system according to the present invention includes a 3 step design using an air sensor to determine air cleaning cycle, and an air intake port with specular reflective surfaces in the inside to provide a reflective element to reflect UV light into the airborne particulates thereby killing 99% of the bacteria and fungi before entering an electrified gravity fed fluid filament air filter which collects the dead bacteria and fungi and settles in a collection reservoir. The fluid in the reservoir is then further filtered to clean the fluid for reuse in the automated air cleaning system.

7 Claims, 4 Drawing Sheets

(56) References Cited

U.S. PATENT DOCUMENTS

| | | | |
|---|---|---|---|
| 5,945,004 A | 8/1999 | Ohira et al. | |
| 9,096,450 B2* | 8/2015 | Andrews | C02F 1/4672 |
| 2005/0029174 A1 | 2/2005 | Collins | |
| 2009/0148342 A1* | 6/2009 | Bromberg | C11D 3/48 |
| | | | 424/661 |
| 2011/0309032 A1 | 12/2011 | Maeki | |
| 2012/0020832 A1* | 1/2012 | St. Onge | F24F 8/26 |
| | | | 422/4 |
| 2014/0356229 A1* | 12/2014 | Farren | A23L 3/28 |
| | | | 250/492.1 |
| 2016/0041074 A1 | 2/2016 | Pliskin | |
| 2017/0050046 A1* | 2/2017 | Walder | A61N 5/062 |
| 2019/0063763 A1* | 2/2019 | Kleinberger | B01D 46/521 |
| 2019/0133391 A1* | 5/2019 | Khazaieli | D06F 58/203 |
| 2019/0209806 A1* | 7/2019 | Allen | H04L 12/2829 |
| 2020/0137964 A1* | 5/2020 | Bouchard | A01G 22/00 |
| 2020/0230273 A1* | 7/2020 | Farren | A61L 2/24 |
| 2021/0356153 A1* | 11/2021 | Nesler | F24F 11/46 |
| 2022/0413166 A1* | 12/2022 | Saccomanno | G01T 1/02 |
| 2023/0211030 A1* | 7/2023 | Lloyd | A61L 2/18 |
| | | | 422/28 |

OTHER PUBLICATIONS

Written Opinion of PCT/US2020/051470 dated Feb. 5, 2020 [PCT/ISA/237].

* cited by examiner

METHODS OF AUTOMATED GARBAGE CHUTE AIR EVACUATION TO IMPROVE AIR QUALITY

BACKGROUND OF THE INVENTION

Waste management in large buildings with garbage chutes utilize collection rooms located at the base of the garbage chute whereby building tenants discard their waste on each floor of the high rise building. Said waste travels down the chute to the collection room and is discarded in a waste bin. Usually this waste has an unpleasant smell or odor which can cause health issues to humans due to the various proteins that become airborne.

A human who senses the unpleasant odor will usually manually turn on an evacuation fan which draws the odor out of the collection area where it is concentrated and ejects it into the environment where it mixes with the air in the surrounding area and becomes diluted or lowers the parts per million of airborne proteins.

Air pollution sensors are devices that detect and monitor the presence of air pollution in the surrounding area. They can be used for both indoor and outdoor environments. Although there are various types of air pollution sensors, and some are specialized in certain aspects, the majority focus on five components: ozone, particulate matter, carbon monoxide, sulfur dioxide, and nitrous oxide. The sensors were very expensive in the past, but with technological advancements these sensors are becoming more affordable and more widespread throughout the population. These sensors can help serve many purposes and help bring attention to environmental issues beyond the scope of the human eye.

The EPA maintains a repository of air quality data through the Air Quality System (AQS), where it stores data from over 10,000 monitors in the United States alone. Scientific evidence has indicated that indoor air pollution can be worse than outdoor pollutants in large and industrialized cities. Many products and chemicals used inside the home, for cooking and heating, and for appliances and home décor are primary sources of indoor air pollutants. Everything we use in the home contributes to the pollution, and can possibly degrade the environment. This is because the airborne pollutants settle and stagnate and begin to decay releasing harmful gases, proteins and fungi which become airborne and enter into human lungs causing respiratory illness and health problems. Air pollution is responsible for 7 million premature deaths around the world each year. When pollutants enter the body through our respiratory system, they can be absorbed in the blood and travel throughout the body, and can directly damage the heart and other vital organs.

Due to concentrations of these pollutants in garbage collection rooms, individuals who service them are at risk of long term health risks from exposure. A need therefore exists to solve two basic issues whereby humans are not subject to concentrated airborne proteins which can be harmful to their health and also clean up the air particles prior to ejecting the air into the environment. Garbage waste byproducts of airborne pollutants are made up of complex mixtures of extremely small particles and liquid droplets. Particle pollution is made up of a number of components, including acids (such as nitrates and sulfates), organic chemicals, metals, and soil or dust particles A pile of garbage contains numerous decaying substances such as diapers, rotting fish, meat and vegetables, various expired products and more. Bacteria present in the air, and in the garbage, degrade the garbage and release different gases such as ammonia, carbon dioxide and methane. Also, some of the contents in the garbage react with each other and release gases such as oxides of sulphur and nitrogen. Burning garbage releases the very poisonous carbon monoxide gas in the air so disposal utilizing trash burning is not a viable solution.

"Good" Air Quality Index (AQI) is 0 to 50. Air quality is considered satisfactory, and air pollution poses little or no risk. "Moderate" AQI is 51 to 100. Air quality is acceptable; however, for some pollutants there may be a moderate health concern for a very small number of people It will become apparent in this application that sufficient description has been given and other modifications could be made without departing from the scope or spirit of the art.

SUMMARY OF THE INVENTION

According to an exemplary embodiment, a design for Methods of Automated Garbage Chute Air Evacuation to Improve Air Quality is comprised of 7 components, namely a means to sense a first air quality threshold value, a means to convert said threshold value into an action or function, a means for action or function to draw air into a specular reflective intake port or chute, a means to kill bacteria and fungi carried as airborne particulates entering the confines of said intake port or chute, a means to pass the first stage of dead bacteria and fungus particulates into a second stage collection containment device, a means for second stage collection containment device to gather dead bacteria and fungus particulates into a third stage silver lined reservoir containment area, a means to filter the collected dead bacteria and fungus into a singular changeable containment filter for proper disposal of said dead bacteria and fungus which was collected in the third stage containment reservoir A means to sense a first air quality threshold value is comprised of an air particulate sensor whereby said sensor is connected to a processing unit which determines readings generated by said air particulate sensor. Said air particulate sensor may sense a variety of particulates as well as other harmful gases which convert said quantitative values of said particulates and harmful gases to a value corresponding to the parts per billion/million. If the air quality exceeds a threshold value, e.g., 50 AQI, a second action or function begins.

This can be achieved in many ways. According to an embodiment, a MQ135 Air Quality sensor is connected to a Microcontroller unit (MCU) which processes the sensed values generated by said MQ135. An algorithm running in the MCU will determine the threshold and actions to be taken once said preset threshold value is exceeded.

A method to convert said threshold value into an action or function is comprised of an algorithm that converts measurements from the air quality sensor to an integer that is stored temporarily into memory. If this measurement reaches a specific value greater than a preset threshold value, an argument calls an output to begin an action or function corresponding to the air quality sensor measurement. Below is a code example:

```
int relay3= 13;
int relay2= 12;
int relay 1 = 11;
void setup( ) {
  Serial.begin(9600);
  pinMode(relay1, OUTPUT);
  pinMode(relay2, OUTPUT);
  pinMode(relay3, OUTPUT);
```

```
}
void loop( ) {
  float sensor voltage;
  float RS_air; // Get the value of RS via in a clear air
  float R0; // Get the value of R0 via in H2
  float sensorValue;
  /*--- Get an arbitration of data by testing 500 times ---*/
  for(int x = 0 ; x < 500 ; x++)
  {
  sensorValue = sensorValue + analogRead(A0);
  }
  sensorValue = sensorValue/500.0;
  /*------------------------------------------*/
  sensor_voltage = sensorValue/1024*5.0;
  RS_air = (5.0-sensor_voltage)/sensor_voltage; // omit *RL
  R0 = RS_air/9.8; // The ratio of RS/RO is 9.8 in a clear air
  Serial.println(R0);
  delay(2500);
if(R0 > = 51)
{
digitalWrite(relay1, HIGH); // Turn on UV Lamp
delay(1500);
digitalWrite(relay2, HIGH); Turn on Fluid Pumps
delay(1500);
digitalWrite(relay3, HIGH); Turn on Fan now for 5 minutes
delay(1000*60*5); // 5 minute timer and go back and read for another
cycle
}
}
}
```

A means for action or function to draw air into a specular reflective intake port or chute is comprised of a fan which turns on after airborne particulates have been determined to surpass the preset threshold value stored in the arguments of the aforementioned MCU algorithm. The first air particle sensor detects airborne particulates and converts the sensed elements to an electric value between 0-5 Volt in 1024 increments. Once this value surpasses 50 parts per million, relays turn on a series of components used to usher in the air pollutants into a chamber. This chamber is made of a specular reflective material which can reflect light. This specular reflective surface acts as an even distributor of bouncing UV light rays which collide with bacteria and fungi airborne particulates killing them on contact. The air particulate intake port may be made of or include a shiny mirror like reflective surface coated to prevent the collection of bacteria from forming on the surface.

A method to kill bacteria and fungi carried as airborne particulates entering the confines of the said intake port or chute is comprised of a UVC light which is part of the ultraviolet light spectrum and emits a high frequency of UV light that makes it extremely effective at killing bacteria, viruses, mold and other pathogens. Killing bacteria with UV light requires the use of germicidal wavelengths of 185-254 nanometers (nm). Ultraviolet germicidal irradiation (UVGI) is a disinfection method that uses short-wavelength ultraviolet (UV-C) light to kill or inactivate microorganisms by destroying nucleic acids and disrupting their DNA, leaving them unable to perform vital cellular functions.

In case of rapidly moving air, in air ducts for example, the exposure time is short so the UV intensity must be increased by introducing multiple UV lamps or even banks of lamps. According to an embodiment, the air duct utilizes a specular reflective trougher which reflects the concentrated UV light into the path of the oncoming airborne pathogens. The fan pulls the air through the internally specular reflective octagon shaped tube (tube with 45 degree angles) into a fan duct which is slowed down due to a fluid soaked air filter used to collect the dead bacteria or fungus. This fluid soaked air filter also acts as a barrier to create turbulence or back pressure in the intake port slowing the air particulates down and giving the high intensity UV lamps time to kill all airborne bacteria and fungi particulates.

A means to pass the first stage of dead bacteria and fungus particulates into a second stage collection containment device is comprised of a filter which is soaked with fluid gravity fed from the top whereby a pump in a containment reservoir pumps fluid from said reservoir to the top dispersing tube which sprays fluid on the top of the air filter. This fluid then soaks said filter and the excess runs off into the fluid containment reservoir. The fluid mechanism is charged with ions which cause particles to attract to them. As the gravity pulls the fluid containing the particulates down to the fluid containment reservoir, it leaves fresh fluid which follows gathering more particulates and flowing to the fluid containment reservoir.

Cellular pavementing with the surface of the said filter will introduce said air borne particulates to an antibiotic solution containing disinfectants which kill germs on contact whereby said fluid falls to a collection containment area via gravity. Clean air passes through said filter replacing the airborne particulate saturated air thus cleaning said air to a safe AQI level making humans and the environment more hospitable or safer.

A means for second stage collection containment device to gather dead bacteria and fungus particulates into a third stage silver lined reservoir containment area is comprised of a self-filling fluid reservoir containing a fluid level limiting device held within a fluid containment area. Said fluid containment area is lined in sliver coating which acts as a secondary disinfectant which may kill any germs that have begun DNA recombination which is a phenomenon known as light and dark repair. This is a photoreactivation and base excision repair, respectively, in which a cell can repair DNA that has been damaged by the first UV light in the first particulate entry tube.

By lining the third element fluid containment are with silver and providing a fourth element of solid block dissolvable disinfectant components, the fluid carrying the bacteria to the fluid containment area will further lyse said bacteria and fungi thus killing any remaining bacteria and reducing the bacterial exhaust to an acceptable range safe for breathing by humans and improving the environment's overall air quality index (AQI).

A means to filter the collected dead bacteria and fungus into a singular changeable containment filter for proper disposal of said dead bacteria and fungus which was collected in the third stage containment reservoir is comprised of a fluid filter whereby fluid in the fluid containment area pumps said fluid into a filter component which acts as a filter for particulates using a fluid cleaning system sufficient to ensure excessive bacteria and fungi buildup in said fluid containing area. The fluid containing area will contain fluid which is filled with collected dead particulates and perhaps a very small percentage of live particulates. Fluid filters use two different techniques to remove particulates. Physical filtration means strains water to remove larger impurities. In other words, a physical filter is a sieve otherwise known as a piece of thin gauze or a very fine textile membrane. Another method of filtering is chemical filtration which involves passing water through an active material that removes impurities chemically as they pass through. According to an embodiment, both straining and chemical filtration are utilized to clean said fluid in the fluid containment area.

Therefore, from the foregoing, it is a general object of the present invention to provide a novel garbage collection room air quality cleaning system and method and related components and processes. Other and further objects, features and advantages of the present invention will be readily apparent to those skilled in the art when the following description of the preferred embodiments is read in conjunction with the accompanying drawings.

DETAILED DESCRIPTION OF EMBODIMENTS

Figure 1:
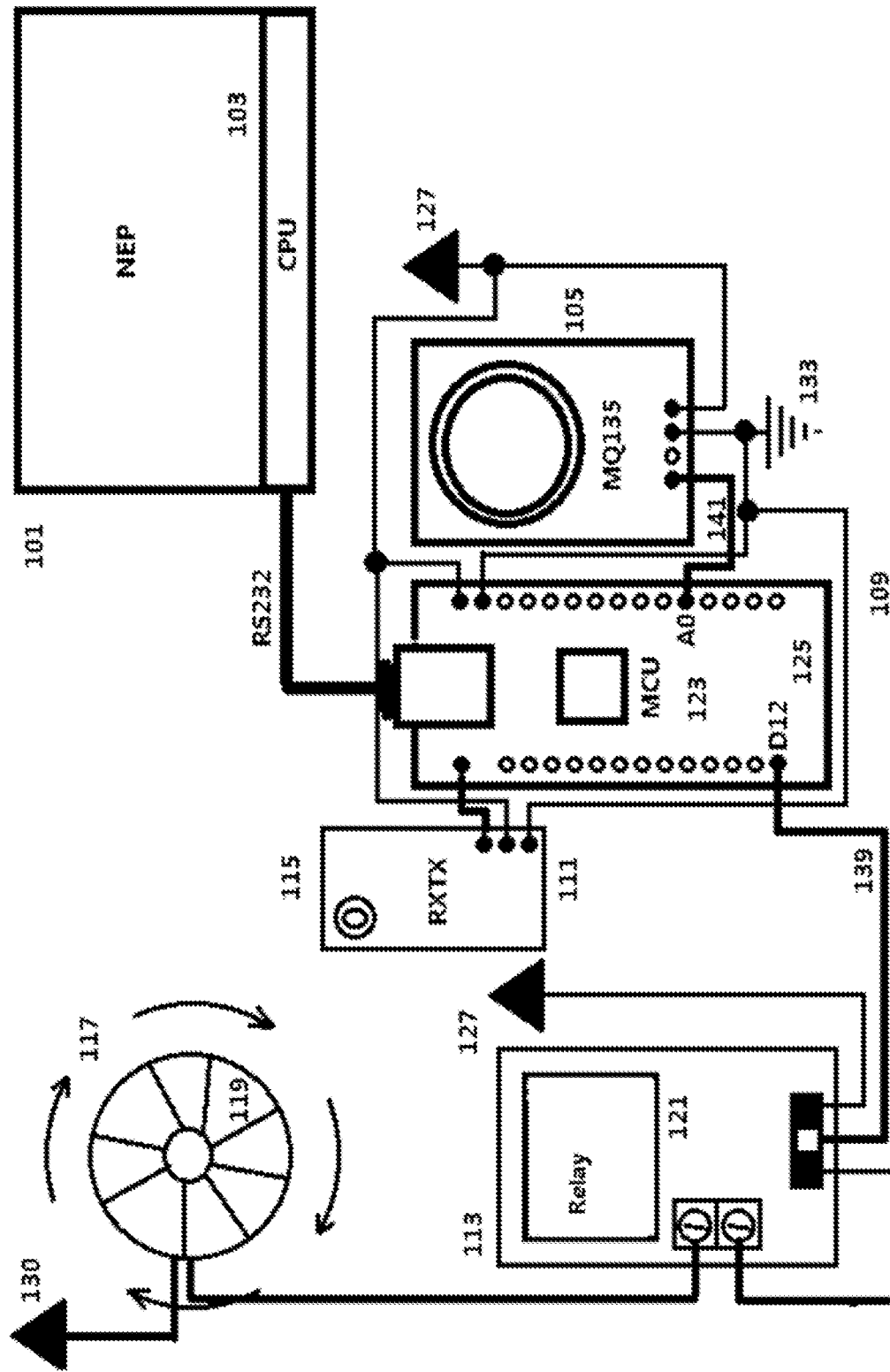
FIG. 1 is a schematic diagram of an air quality cleaning system including a Microcontroller Unit (MCU) a MQ135 Air Quality Sensor, a motorized fan, a PC for intelligent integration of control software, a relay representing actions or functions from the results collected from the MQ135 to the MCU and a wireless control option.

Airborne particulates are generated in high concentrations in garbage collection rooms found beneath garbage chutes where tenants in the above floors utilize a chute to drop their waste. As the waste falls inside the garbage chute, it collides with areas meant to slow the fall of the garbage. These areas are angular which are impacted by said garbage waste. In many cases, the garbage waste is within a bag that breaks such that the waste is separated from said bag allowing waste material containing rotting or decaying bacteria and fungus to spread or be exposed. In this application we propose a simple method to detect particulates and gases released by said waste bacteria and fungi and filter it from the air to ensure a more safe and healthy environment for waste collection facilities.

According to an embodiment, an air quality improvement or cleaning system contains an air quality sensor. In the present embodiment, an MQ135 is exemplified as an air quality sensor. The MP135 is connected to a MCU which handles conversion of sensor readings to data and then acts upon preset threshold variables. Once a preset threshold has been exceeded, the MCU activates a series of actions which allow proper operation of an automated garbage chute air evacuation system according to an embodiment. This includes a first element high powered UVC lamp which operates a light wave between >150 and <300 nm respectively which is optimum light spectrum for disinfectant of bacteria and fungi, a second angular tubing with specular reflective surfaces which has sufficient angles to refract light waves covering all areas of said angular tubing, a third induction fan to decrease pressure in said specular reflective coated angular tubing which draws outside air containing airborne bacteria and fungi into said angular tubing whereby said air containing airborne particulates is bombarded by the high powered UVC light rays, a fourth element being a filter containing a fluid which has a disinfectant (Chemical) that further ensures both airborne particulates of bacteria and fungi are collected or captured, and a fifth element which collects said fluid containing said disinfectant and stores said disinfected fluid in a silver lined container which further ensures all living harmful bacteria and fungi are disinfected.

The MQ-135 Gas sensor is used in air quality control equipment and is suitable for detecting or measuring of NH3, NOx, Alcohol, Benzene, Smoke, CO2 and other harmful particulates. MQ-135 gas sensor applies SnO2 which has a higher resistance in the clear air as a gas-sensing material. When there is an increase in polluting gases, the resistance of the gas sensor decreases. This value can be determined by utilizing a MCU where the values are converted to an integer and compared to a threshold.

```
int sensorValue;
int digitalValue;
void setup( )
{
Serial.begin(9600); // sets the serial port to 9600
pinMode(13, OUTPUT);
pinMode( 3, INPUT);
}
void loop( )
{
sensorValue = analogRead(0); // read analog input pin 0
digitalValue = digitalRead(2);
if(sensorValue>51)
{
digitalWrite(13, HIGH); // Action or function if value exceeds the
threshold
delay(1000*60*5); // Runs action for 5 minutes and then rechecks air
quality status
}
else
digitalWrite(13, LOW); //Action stopped
Serial.println(sensorValue, DEC); // prints the value read to a computer
(101 fig l)
Serial.println(digital Value, DEC);
delay(1000); // wait 100ms for next reading
}
```

In the code, the MCU reads the Analog input from the MQ135 10 times per second. This constant reading of the concentration of air quality will raise and lower in the garbage chute collection room according to the proposed cleaning device activation. When the code detects 50 parts per million (50 ppm) or more, the Relay (pin 13) activates for 5 minutes. This relay represents actions taken once the threshold of airborne contaminants is detected to be above the AQI (Air Quality Index) of 50.

The actuation of the relay can set off a series of events as per requirement of said air decontamination process. These events include a UVC lamp to provide the proper range of UV light to disinfect a first stage of collected airborne contaminants, a wet filter which further contains proper chemicals to further disinfect and collect contaminants and a fluid collection bin which further contains a silver lining which also acts as a disinfectant for killing germs collected in the wet filter stage of decontaminating the air to improve said air quality index (AQI).

FIG. 1 shows a schematic diagram containing a first element of a MQ135 (105) connected by an analog bus (141) which provides a variable sensor reading to the MCU (125). If said variable sensor reading reaches a threshold preset value, the MCU (125) passes a high output voltage to the Relay Controller (121) which causes the fan (119) to turn on. This starts the air flow. A wireless (115) or wired bus (RS232) can link to a PC which monitors information of the air quality improvement application according to embodiments.

The MQ135 operates on 5V which is connected to VCC (127) and GND (133) where all elements share like voltages. Said PC contains relevant Natural Event Processing (NEP) logic to monitor, control and report actions of hardware through a remote server application or network.

Figure 2:
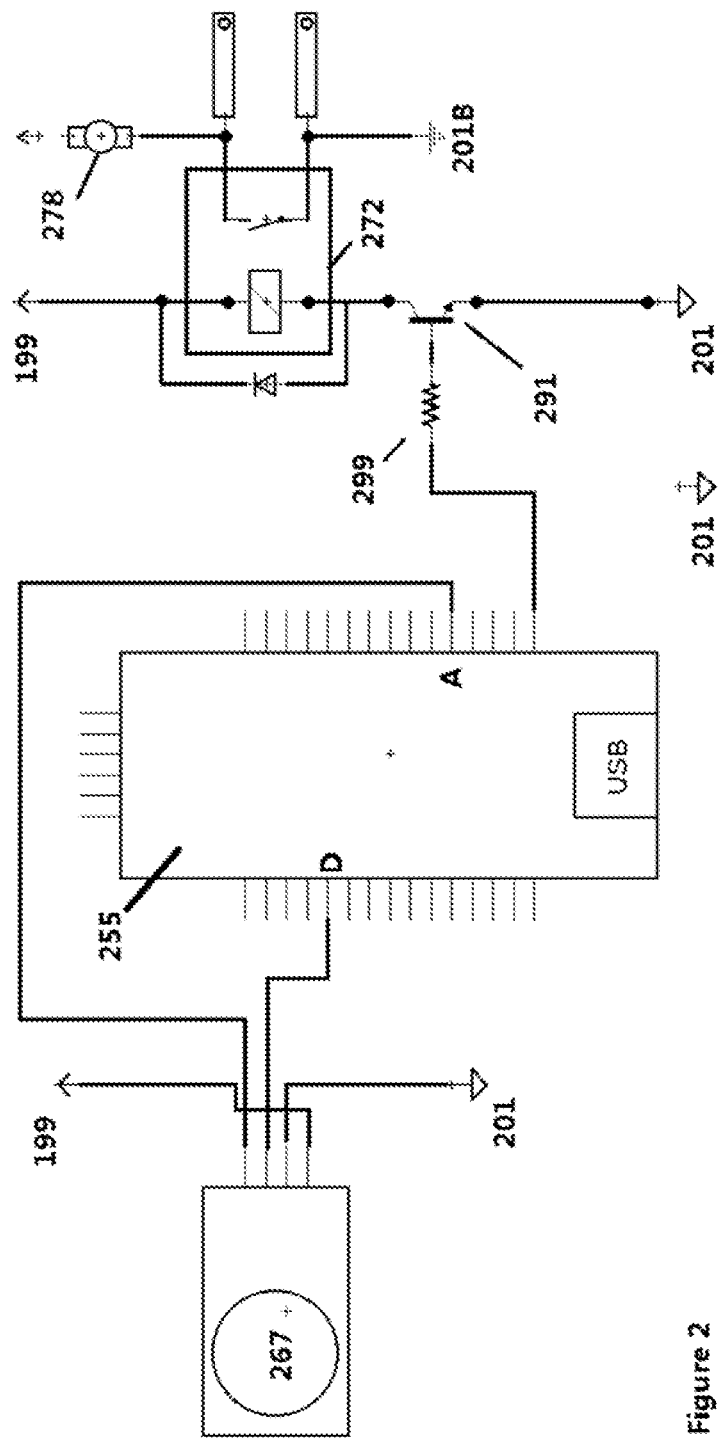
FIG. 2 is a simplified drawing of a schematic diagram containing basic elements of a MQ135 for air quality sensing, a MCU for processing and a Relay for acting upon air quality threshold events.

FIG. 2 is a fundamental schematic diagram showing the basic essentials of the circuit to actuate an event using an Air Quality Sensor (267) connected to both digital input and analog input of the MCU (255) which is connected to a relay (272) where contactors of said relay are connected to a motor which controls a fan, a UVC lamp and necessary pumps to control proper fluid flow (Not Shown). The Relay, MCU (255) and air quality sensor (267) is connected to VCC (199) and GND (201).

Figure 3:
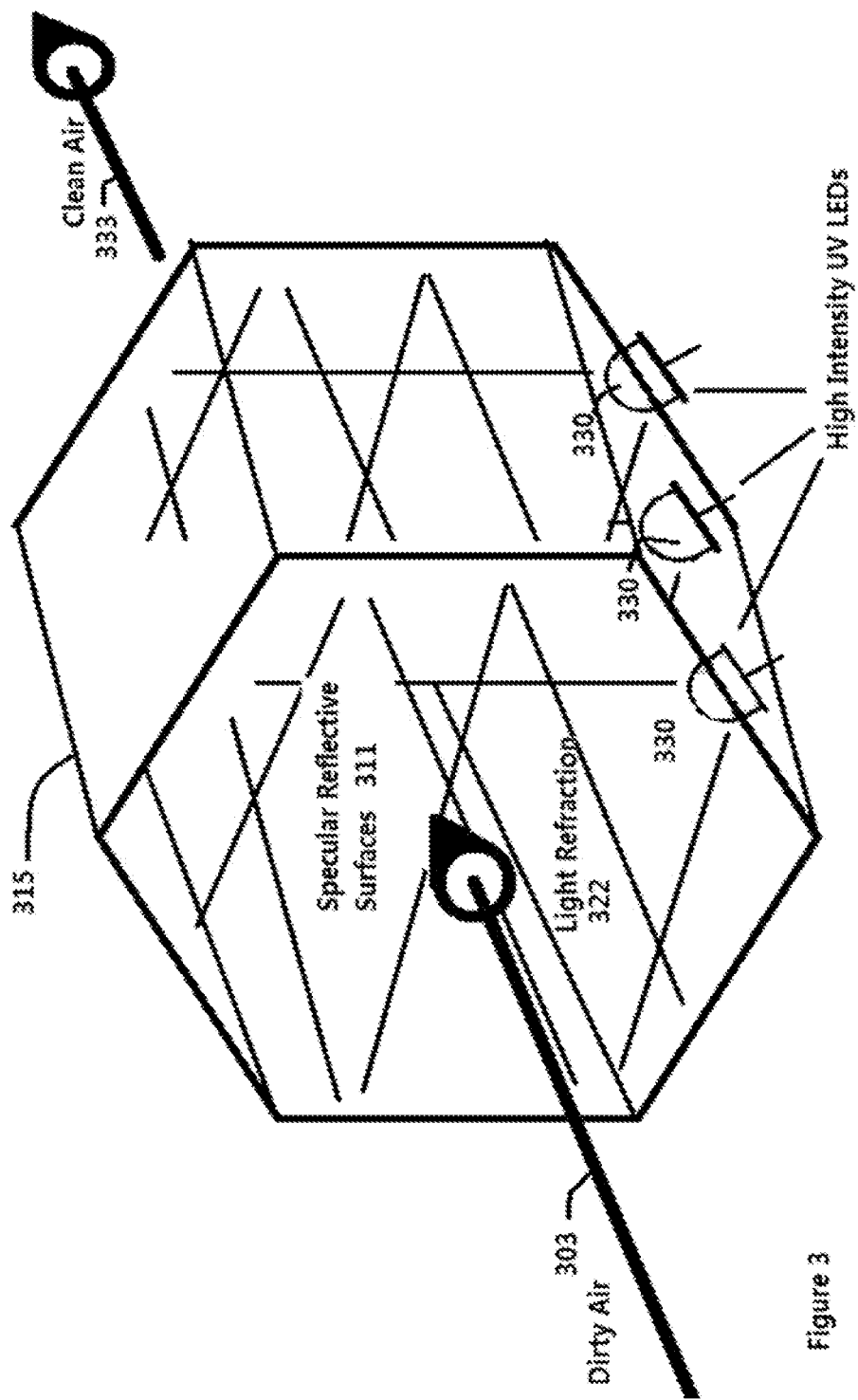
FIG. 3 is a 3D rendering of the intake tube with specular reflective coatings showing UVC light refracting from the angular tubing refraction angles.

FIG. 3 shows dirty air (303) entering the opening of an angular tubing (315) which contains a specular reflective coating (311) whereby UVC light rays (322) bounce off various angles provided by the reflective surface (311) of the angular tubing (315). Said angular tubing contains a UVC light source (330) which provides the interior of said angular tubing (315) with sufficient UVC light rays (322) which is refracted off the specular reflective walls (311) of the angular tubing port (315). The exhaust air (333) is a clean air which exits the UVC chambered (315) specular reflective (311) coated angular intake port (315).

Figure 4:
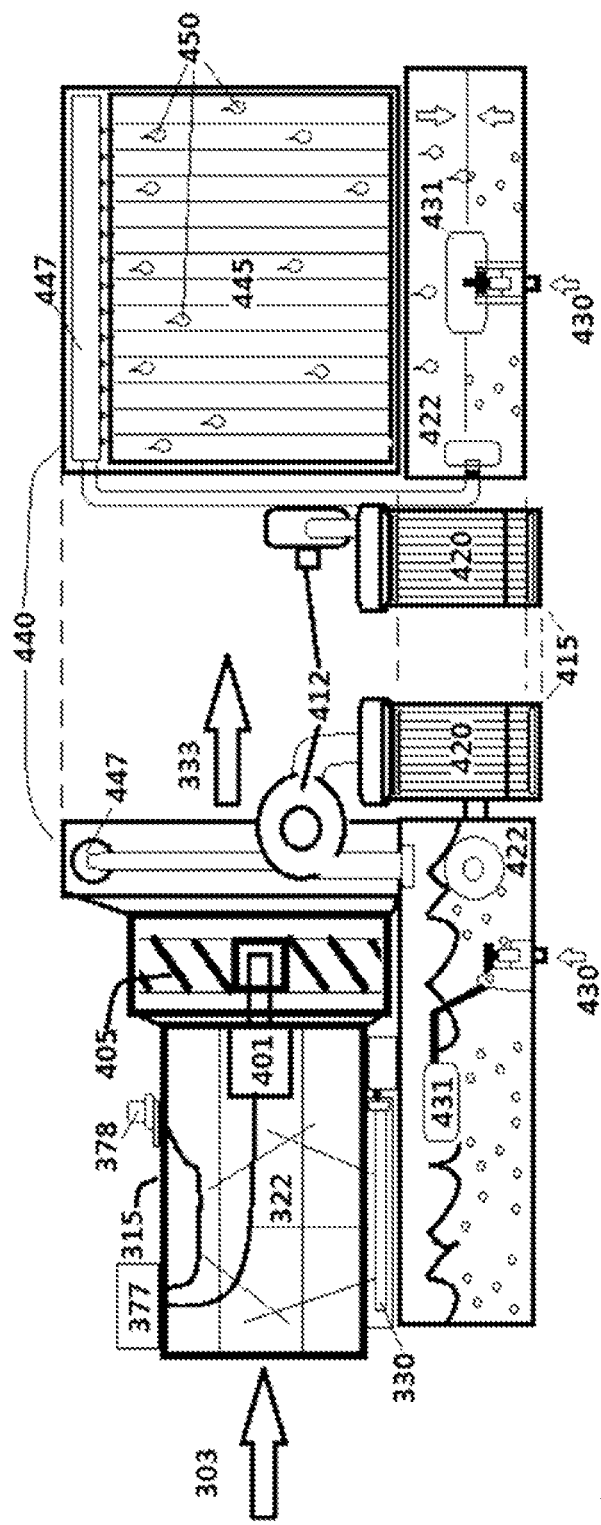
FIG. 4 is a drawing of an air quality management system containing a first MQ135 sensor, an intake angular tubing intake chute, a fan, a filter component and a fluid storage component and a filter to clean said fluid for easy maintenance.

FIG. 4 is s combined system containing a first air quality sensor (378) which resides external to the intake port (315) where incoming dirty air (303) containing airborne particulates enters internally in said specular reflective (322) angular tubing (315) whereby said air particulates containing bacteria and fungi are bombarded with a UVC light (330) where said UVC light rays bounce off specular reflective coatings (322) inside the angular tubing (315). A MCU (377) provides control for the external peripherals of the fan (401), first fluid pump (412) which pumps disinfectant fluid in fluid chamber (431) which is silver lined to further decontaminate said living bacteria and fungi. A pump (422) to push fluid to the top of the wet filter (445) whereby gravity draws droplets containing dead bacteria and fungi back into the reservoir (431). A fluid intake is controlled by a float system (430) which keeps the fluid at a proper level. Finally, a filter (420) in a filter chamber (415) is utilized to filter any decontaminants found in the fluid which captures said harmful particulates and can easily be discarded by opening the said filter chamber (415) and removing the fluid filter (420) and replacing it with a new one on a periodic basis. Cleaned air (333) exits the wet filter.

What is claimed is:

1. A garbage collection room automated air quality cleaning system which monitors waste collection room airborne particulates, said system comprising:
    an air quality sensor configured to sense particulates in air;
    a microcontroller unit (MCU) configured to, based on the sensed particulates:
        activate or deactivate a UVC light source contained within a specular reflective angular tubing which refracts UVC light rays emitted by the UVC light source in concentration to disinfect said air,
        activate or deactivate a fan source which is located behind a wet filter to provide back pressure stagnating airflow of said air,
        activate or deactivate a disinfectant fluid flow which keeps said wet filter saturated, a fluid reservoir to capture excess disinfectant fluid and a changeable filter which keeps said fluid reservoir clean.

2. The system according to claim 1, further comprising means to perpetually fill fluids lost in evaporation of a disinfecting cycle.

3. The system according to claim 2, wherein said perpetually filled fluids are chemically treated with a disinfectant used in killing germs and/or pathogens.

4. The system according to claim 1, wherein said UVC lamp is contained within an angular specular reflective coated intake port.

5. The system according to claim 1, wherein said MCU is configured to activate back pressure stagnating airflow caused by said wet filter to ensure proper stagnation or restriction of airflow and timing of UVC light exposure to airborne bacteria and fungi.

6. The system according to claim 1, wherein said wet filter is porous to allow passage of air while providing both sufficient means free path (MFP) of air flow and cellular pavementing with increased surface area.

7. The system according to claim 6, wherein said cellular pavementing is harmful bacteria and fungi which lyse due to primary interaction of UVC light exposure and disinfectant.

\* \* \* \* \*